United States Patent [19]

Gropper et al.

[11] Patent Number: 5,540,220
[45] Date of Patent: Jul. 30, 1996

[54] PRESSURE-LIMITED, TIME-CYCLED PULMONARY VENTILATION WITH VOLUME-CYCLE OVERRIDE

[75] Inventors: Charles M. Gropper, Yorba Linda; Raymond A. Ellestad, Rialto, both of Calif.

[73] Assignee: Bear Medical Systems, Inc., Riverside, Calif.

[21] Appl. No.: 351,833

[22] Filed: Dec. 8, 1994

[51] Int. Cl.⁶ .................................................. A61M 16/00
[52] U.S. Cl. .............................. 128/204.23; 128/204.26; 128/205.25; 128/204.21
[58] Field of Search ................................. 128/719, 716, 128/720, 204.18, 204.21, 204.26, 205.14, 205.24, 205.18, 205.25, 204.23

[56] References Cited

U.S. PATENT DOCUMENTS

| Re. 29,778 | 9/1978 | Stewart | 128/204.24 |
|---|---|---|---|
| 3,523,527 | 8/1970 | Foster | 128/145.6 |
| 3,633,576 | 1/1972 | Gorsuch | 128/145.8 |
| 3,729,000 | 4/1973 | Bell | 128/145.6 |
| 3,916,890 | 11/1975 | Freeman | 128/205.14 |
| 3,961,627 | 6/1976 | Ernst et al. | 128/145.8 |
| 3,972,327 | 8/1976 | Ernst et al. | 128/145.8 |
| 4,057,059 | 11/1977 | Reid, Jr. et al. | 128/204.24 |
| 4,227,519 | 10/1980 | Warnow et al. | 128/205.24 |
| 4,351,344 | 9/1982 | Stenzler | 128/720 |
| 4,527,557 | 7/1985 | DeVries et al. | 128/204.23 |
| 5,069,220 | 12/1991 | Casparie et al. | 128/719 |
| 5,107,831 | 4/1992 | Hälpern et al. | 128/204.26 |
| 5,129,390 | 7/1992 | Chopin et al. | 128/204.21 |

OTHER PUBLICATIONS

Depuis, Y., "Ventilators: Theory and Clinical Application," (C. V. Mosby Co., N.Y., 1986) pp. 126–140 and 513–522.
Brochure, "The Bear Cub Enhancement Module: It synchronizes ventilation for less work in breathing," 1994.

Primary Examiner—Edgar S. Burr
Assistant Examiner—Eric P. Raciti
Attorney, Agent, or Firm—Klein & Szekeres

[57] ABSTRACT

A pressure-limited, time-cycled pulmonary ventilator includes a pressurized gas system that supplies respiratory gas to a patient at a selected inspiratory flow rate; an exhalation valve that (a) opens an expiratory flow path in response to the elapsing of a selected inspiratory time period, and (b) maintains a selected proximal pressure limit during the inspiratory time period; and a volume-cycle override system that actuates the exhalation valve so as to open the expiratory flow path if the patient's tidal volume reaches or exceeds a selected volume limit during the inspiratory time period. The volume-cycle override system includes a flow sensor that outputs an inhalation flow rate signal. The flow rate signal is integrated to derive a measured tidal volume signal. An operator control produces a volume limit signal, indicating a selected volume limit, that is compared with the measured tidal volume signal to yield a difference signal. The exhalation valve opens the expiratory flow path in response to the difference signal having a value indicating that the measured tidal volume is equal to or greater than the selected volume limit, as long as the proximal pressure exceeds a selectable reference pressure. An exhalation control system provides a first reference pressure at the beginning of the inspiratory time period, and a second reference pressure at the end of the inspiratory time period, or when the difference signal indicates that the measured tidal volume is equal to or greater than the selected volume limit, whichever first occurs.

28 Claims, 6 Drawing Sheets

PRESSURE-LIMITED, TIME-CYCLED PULMONARY VENTILATION WITH VOLUME-CYCLE OVERRIDE

BACKGROUND OF THE INVENTION

This invention relates to the field of mechanical pulmonary ventilation. In particular, the present invention relates to a method and apparatus for pulmonary ventilation support which represents an improvement in the mode of mechanical ventilation known as "pressure-limited, time-cycled" ventilation.

Pressure-limited, time-cycled mechanical ventilation is well known in the art. Briefly described, in this mode of ventilation, a pressure limit is applied, during the inspiratory phase of respiration, to limit the peak inspiratory pressure to a selected (adjustable) maximum value. Once this maximum pressure value is reached, airway pressure is held at that value for the remaining duration of the selected (adjustable) inspiratory time period, during which gas continues to flow to the patient, albeit at a decelerating flow rate as the lungs fill. At the end of the selected inspiratory time period, the exhalation valve of the ventilator is opened for a selected (adjustable) expiratory time period, allowing exhalation either to ambient pressure, or to a positive end expiratory pressure ("PEEP").

Pressure-limited, time-cycled ventilation is distinct from volume-cycled ventilation, in which the inspiratory flow is stopped after a preselected tidal volume is delivered (to the patient and to the patient circuit), independently of peak inspiratory pressure, inspiratory time, and inspiratory flow rate.

Pressure-limited, time-cycled ventilation is often used for infants and neonates, particularly patients with hyaline membrane disease. An advantage of this mode of ventilation is that the pressure limitation feature reduces the risk of barotrauma.

The treatment of neonates with hyaline membrane disease and other respiratory disorders attributed to incomplete pulmonary development usually includes the administration of surfactants to the patient's lungs. The use of a surfactant typically results in an increase in the compliance of the lungs, resulting in greater tidal volume delivered to the lungs at any given peak inspiratory pressure. Consequently, to prevent over-expansion of the lungs (pulmonary hyperdistention), the peak inspiratory pressure limit must be periodically lowered as the surfactant takes effect. Recently, new surfactants and surfactant delivery methods have become available that produce dramatically more rapid and pronounced increases in compliance than have heretofore been possible, thereby requiring more rapid and frequent adjustments of the peak inspiratory pressure limit. Failure to adjust this limit properly could result in the delivering of a larger tidal volume to the patient, at a selected pressure limit, than the patient can bear without injury.

Mechanical ventilators in the prior art have not adequately addressed the above-described problems associated with changes in lung compliance, and therefore they have not obviated the need for frequent monitoring of tidal volume and adjustment of the pressure limit to compensate for these changes.

One approach to solving the above-described problems would be to provide a pressure-limited, time-cycled ventilator with a volume-cycling capability. The prior art, however, has viewed time-cycled, pressure-limited ventilation and volume-cycled ventilation as alternative ventilatory support modes, to be used separately, and not together in what may be termed a complementary sense. In other words, while the prior art has recognized the respective benefits of these two modes independently applied, it has not recognized any need for, or benefit of, employing a ventilatory support mode in which any given machine-delivered inspiratory breath can be both pressure-limited and either time-cycled or volume-cycled.

A survey of the relevant prior art reveals the following examples:

U.S. Pat. No. 3,523,527—Foster discloses a time-cycled ventilator which delivers an inspiratory breath for a preselected inspiratory time period, unless, before the expiration of the time period, a preselected pressure limit or a preselected volume limit is reached. In other words, the inspiratory flow is stopped whenever the first of three parametric limits (time, pressure, or volume) is reached; for any given breath, the ventilator may therefore be time-cycled, pressure-cycled, or volume-cycled. The ventilator is not pressure-limited, in that the inspiratory phase is not continued at the maximum pressure until the inspiratory time period has elapsed; the inspiratory phase is simply terminated.

U.S. Pat. No. 3,633,576—Gorsuch describes a volume-cycled ventilator that employs a time-cycled, pressure-limited ventilator as a pressurized gas source.

U.S. Pat. No. 3,729,000—Bell discloses a volume-cycled ventilator that maintains a constant delivered volume in the face of changing system compliance.

U.S. Pat. No. 3,961,627—Ernst et al. discloses a ventilator with pressure regulation during a first part of the inspiratory period, followed by flow regulation during a second part of the inspiratory period. A pressure limit and a flow rate limit are thus applied sequentially within an inspiratory time period, with the object of delivering the desired volume at the end of the inspiratory period.

U.S. Pat. No. 3,972,327—Ernst et al. discloses a volume-cycled ventilator with a pressure-limiting override feature. The ventilator can switch from flow rate-regulated inspiratory flow to a pressure-limited flow if, during inspiration, the buccal pressure, or the rate of increase of buccal pressure, exceeds preselected limits.

U.S. Pat. No. 5,129,390—Chopin et al. discloses a volume-cycled ventilator that establishes an optimum minute volume, with a set limit for proximal pressure ("airway passage pressure").

It will thus be appreciated that none of the above-referenced prior art patents suggests a time-cycled, pressure-limited ventilator with a volume cycle override that can be applied simultaneously with the pressure limit, to provide a machine-delivered inspiratory breath that is both pressure-limited and either time-cycled or volume-cycled.

SUMMARY OF THE INVENTION

Broadly, the present invention is an improved pressure-limited, time-cycled ventilator, wherein the improvement comprises means for applying a preselected tidal volume limit as a back-up or override limit, in addition to, and simultaneously with, the preselected pressure limit.

More specifically, the invention is embodied in a ventilator that provides a selectable constant inspiratory flow rate to a patient. The proximal pressure of the patient is monitored during inspiration, and a proximal pressure signal is generated. A pressure control mechanism includes an exhalation valve that remains closed during the inspiratory phase, until the proximal pressure, as indicated by the proximal pressure signal, reaches a preselected limit, at which point the exhalation valve opens sufficiently to vent pressure over the limit, thereby maintaining the pressure substantially at the limit. When the preselected inspiratory time period has elapsed, an expiratory phase begins, whereupon the pressure control mechanism opens the exhalation valve to vent expiratory gas either to ambient pressure or to an applied positive end expiratory pressure (PEEP).

The improvement according to the present invention is the addition of means for terminating the inspiratory phase prior to the elapsing of its preselected time period in response to a delivered tidal volume that meets or exceeds a preselected limit, so that the time-cycling function is, in essence, overridden by a volume-cycling function. Viewed another way, the inspiratory phase is terminated either by the elapsing of the preselected inspiratory time period, or by the reaching of the preselected tidal volume limit, whichever first occurs. In either case, the proximal pressure is limited so as not to exceed its preselected maximum.

The above-described improvement is carried out, in a preferred embodiment of the invention, by providing a flow sensor in the patient circuit, between the patient and the ventilator. The flow sensor generates an inhalation flow-indicative signal during inspiration. The inhalation flow-indicative signal has a value that is related to the instantaneous flow rate of the gas inhaled by the patient from the inspiratory gas stream provided by the ventilator. This instantaneous inhalation flow rate value is electronically integrated to obtain a substantially real-time value indicative of the measured instantaneous tidal volume. The measured tidal volume value is periodically compared with an electronically stored tidal volume limit value. If the comparison shows that the measured value is less than the stored limit value, the inspiratory phase is allowed to continue. If, however, the measured value equals or exceeds the stored limit value, the inspiratory phase is terminated, and the expiratory phase is commenced, even if the preselected inspiratory time period has not elapsed. The stored tidal volume limit value may be changed, as desired by the clinician, by an operator control.

As will be more fully appreciated from the detailed description that follows, the subject invention offers all of the well-recognized advantages of time-cycled, pressure-limited ventilation, while also offering the further advantage of a volume-cycling function that can override the time-cycling function, and that is useful in situations in which pulmonary hyperdistention is of concern.

DETAILED DESCRIPTION OF THE PREFERRED EMBODIMENT

Figure 1:
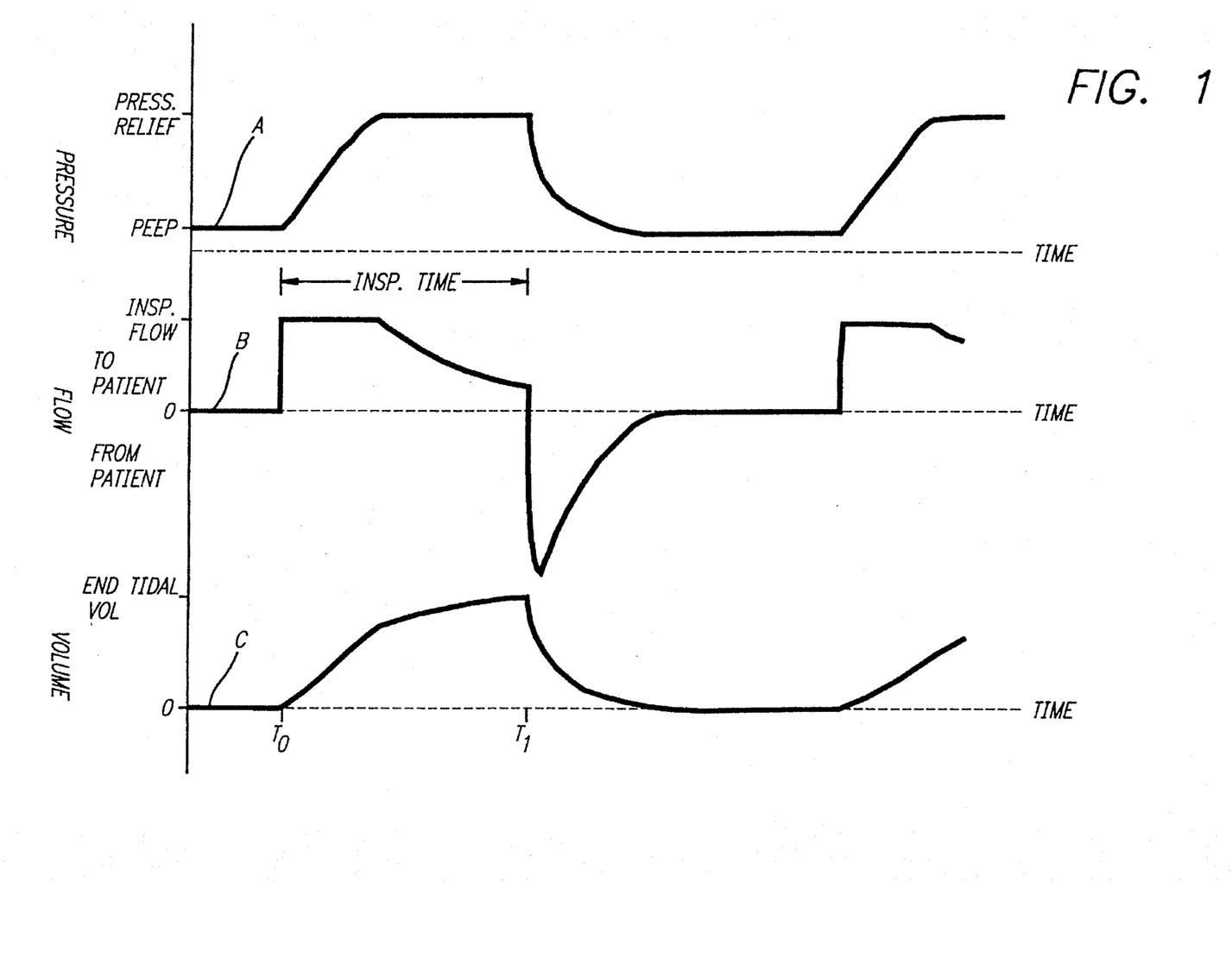
FIG. 1 is a graphical representation of the operation of a pressure-limited, time-cycled ventilator.
Figure 2:
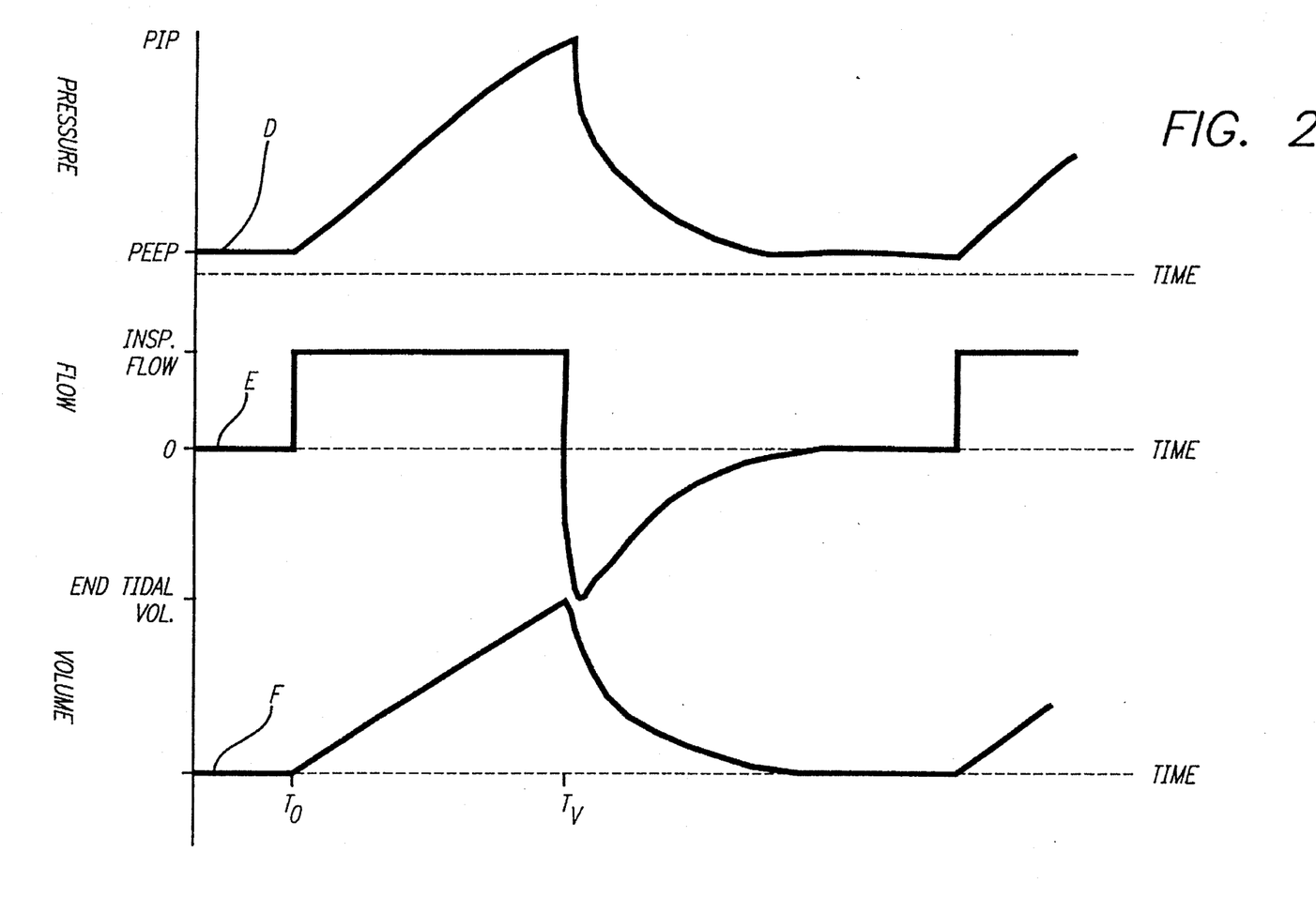
FIG. 2 is a graphical representation of the operation of a volume-cycled ventilator.
Figure 3:
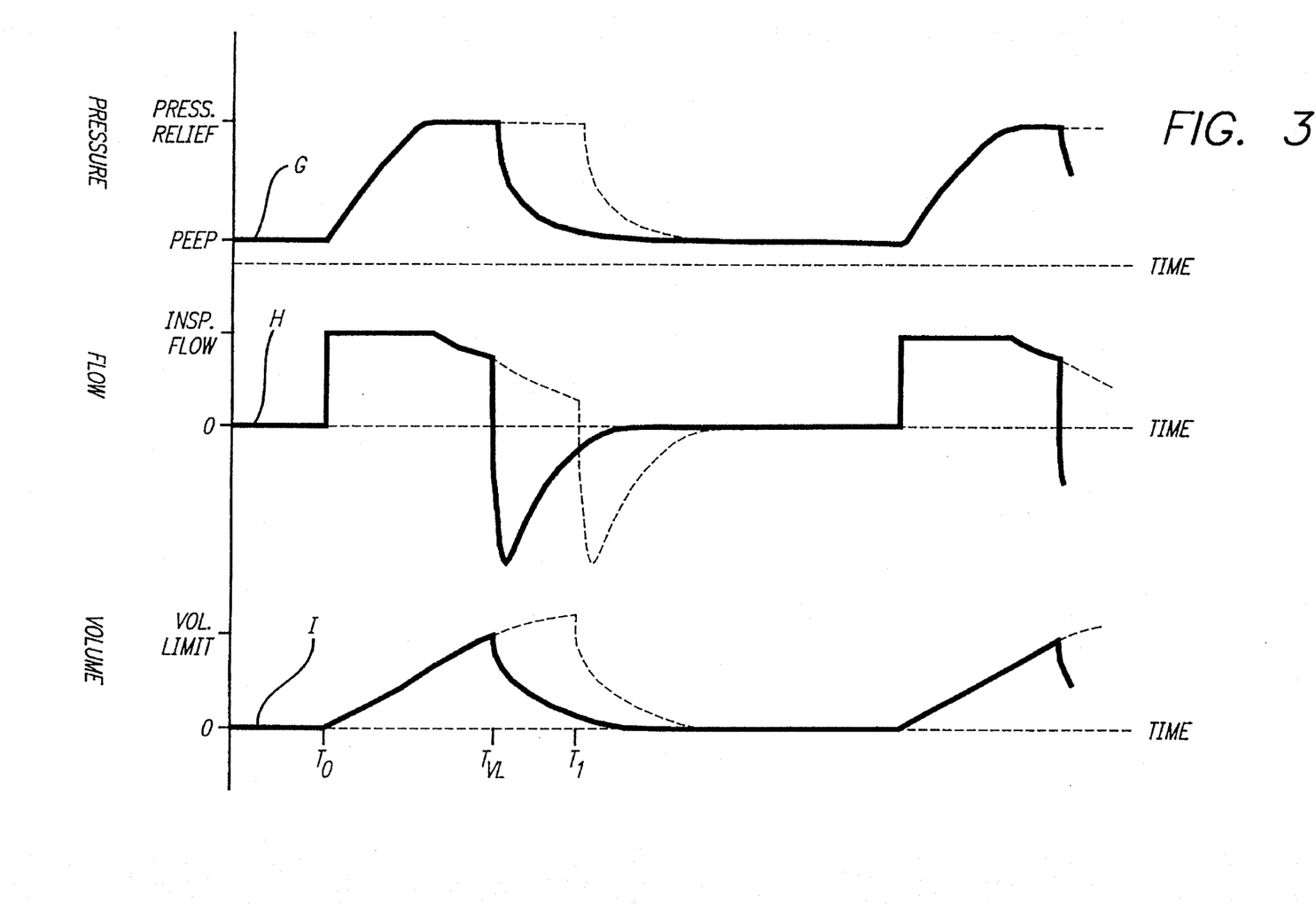
FIG. 3 is a graphical representation of the operation of a pressure-limited, time-cycled ventilator with a volume-cycle override, in accordance with a preferred embodiment of the present invention.

The principles of operation of the present invention are best understood with reference first to FIGS. 1, 2, and 3.

FIG. 1 graphically illustrates the method of operation of a typical pressure-limited, time-cycled ventilator. The uppermost graph A is a graph of proximal pressure versus time; the middle graph B is a graph of respiratory flow rate (at the patient connection) versus time; and the lowermost graph C is a graph of the pulmonary tidal volume versus time. The time period for the inspiratory phase (inspiratory time period) is indicated by the notation "INSP. TIME" on the horizontal (time) axis.

At the beginning of the inspiratory phase, at time $T_0$, the patient's respiratory (inhalation) flow rate almost instantaneously reaches a plateau level, substantially equal to the constant flow rate generated by a continuous flow ventilator. The proximal pressure (which is a function of tidal volume, pulmonary and patient circuit compliance, and, to a lesser degree, inhalation flow rate and airway resistance) quickly increases to its preselected maximum value, or pressure relief level, indicated in FIG. 1 by the notation "PRESS. RELIEF". The proximal pressure is maintained at this pressure relief level by the operation of a pressure relief mechanism, which includes an exhalation valve, as will be described below in conjunction with the description of the apparatus illustrated in FIG. 4. The patient's inhalation gas flow continues, at a declining flow rate, until the end of the inspiratory time period, at time $T_1$. The tidal volume increases throughout the inspiratory period, the tidal volume at the end of the inspiratory phase ("END TIDAL VOLUME") being chiefly a function of the pressure relief level and the compliance of the patient's lungs, with patient airway resistance, gas flow rate, and the length of the inspiratory time period also being factors.

At the end of the inspiratory time period ($T_1$), the exhalation phase is commenced by the opening of the exhalation valve, and the proximal pressure rapidly falls either to ambient pressure, or, as shown in FIG. 1, to a preselected positive end expiratory pressure (PEEP). The gas flow reverses, as shown in graph B, indicating an exhalation flow from the patient through the exhalation valve.

From the foregoing, it can be appreciated that a significant increase in lung compliance (the ratio of tidal volume to transpulmonary pressure, or the increase in pulmonary volume per unit pressure increase) during the inspiratory time period will result in a corresponding increase in the tidal volume during the inspiratory phase. Consequently, the actual end tidal volume might exceed the expected end tidal volume, with a possibility of pulmonary hyperdistention.

FIG. 2 graphically illustrates the method of operation of a typical volume-cycled ventilator. The uppermost graph D is a graph of proximal pressure versus time; the middle graph E is a graph of respiratory flow rate (at the patient connection) versus time; and the lowermost graph F is a graph of the pulmonary tidal volume versus time.

At the beginning of the inspiratory time period ($T_0$), an inspiratory gas flow is generated by the ventilator. The gas flow rate may be a substantially constant flow rate, as represented by the square wave shown in the graph E, or it may be a decelerating flow rate, an accelerating flow rate, or a sinusoidal flow rate. With a constant flow rate, the proximal pressure increases approximately linearly throughout the inspiratory phase to a peak inspiratory pressure ("PIP"). The tidal volume also increases substantially linearly. When a preselected end tidal volume is reached, at a time $T_V$, the inspiratory phase is terminated, and the expiratory phase begins. An exhalation valve is opened, allowing exhalation to ambient pressure, or, as shown in the graph D, a preselected PEEP level.

Thus, as shown in FIG. 2, a volume-cycled ventilator offers a selectable and controllable end tidal volume, but the peak inspiratory pressure may exceed a desired level, unless otherwise limited, for example, by an overpressure relief valve or the like.

FIG. 3 graphically illustrates the method of operation of a pressure-limited, time-cycled ventilator with volume-cycle override, in accordance with the present invention. The uppermost graph G is a graph of proximal pressure versus time; the middle graph H is a graph of respiratory flow rate (at the patient connection) versus time; and the lowermost graph I is a graph of the pulmonary tidal volume versus time. In each graph, the solid curve represents the operation of a pressure-limited, time-cycled ventilator with volume-cycle override, in accordance with the present invention, while the dashed-line curve represents the operation of a conventional pressure-limited, time-cycled ventilator (i.e., without volume-cycle override). Alternatively, the dashed-line curve may represent the operation of a pressure-limited, time-cycled ventilator with volume-cycle override, wherein the volume limit (as will be described below) is not reached during the preselected inspiratory time period.

As with a conventional pressure-limited, time-cycled ventilator, a ventilator in accordance with the present invention generates a substantially constant gas flow rate. The inspiratory time period begins, at a time $T_0$, with the patient's inhalation flow rate almost instantaneously reaching a plateau level that is substantially equal to the ventilator's constant flow rate. The proximal pressure quickly rises to its preselected pressure relief level, at which it is maintained by the pressure control mechanism, as will be described below. The tidal volume also increases, but, if it reaches a preselected volume limit prior to the end of the preselected inspiratory time period (at the time $T_1$), the inspiratory phase is terminated at an earlier time $T_{VL}$. This is accomplished by opening the exhalation valve, thereby initiating the expiratory phase and allowing the patient to exhale to ambient or (as shown in the graph G) to a preselected PEEP.

If, on the other hand, the preselected volume limit is not reached prior to the time $T_1$ that ends the normal inspiratory phase (for example, if the volume limit is set higher than the end tidal volume at the time $T_1$), the ventilator functions as a conventional pressure-limited, time-cycled, ventilator, switching to the expiratory phase at the time $T_1$ that ends the preselected inspiratory time period.

Figure 4:
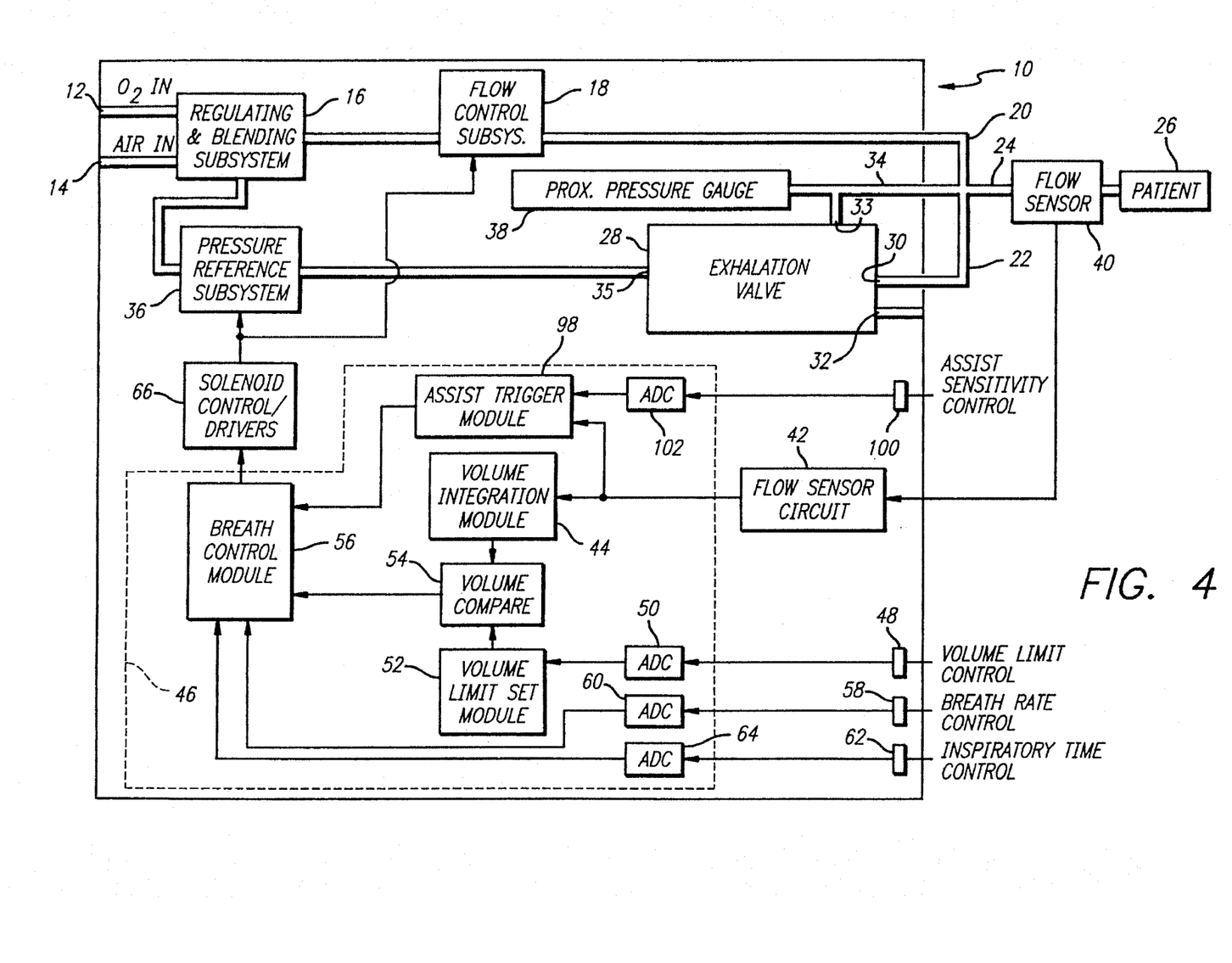
FIG. 4 is a schematic representation of a pressure-limited, time-cycled ventilator with volume-cycle override, in accordance with a preferred embodiment of the present invention.

A preferred embodiment of a pressure-limited, time-cycled ventilator 10 with volume-cycle override is shown schematically in FIG. 4.

The ventilator 10 has a pressurized oxygen inlet 12 and a pressurized air inlet 14, each of which receives its respective gas from a conventional pressurized source (not shown). The air and oxygen are pressure-regulated and blended in selectable proportions in a regulating and blending subsystem 16, of conventional design. The blended respiratory gas is then passed through a flow control subsystem 18 (to be described in detail below) that controls the flow rate of the respiratory gas.

The flow- and pressure-regulated respiratory gas then is passed from the ventilator 10 into a gas conduit forming a patient circuit having an inspiratory leg 20 and an expiratory leg 22. A patient connector 24 at the juncture between the inspiratory leg 20 and the expiratory leg 22 provides fluid communication between the airway of a patient 26 and the patient circuit. The expiratory leg 22 communicates between the patient connector 24 and an exhalation valve 28 in the ventilator 10. The operation of the exhalation valve 28 will be described below.

As will be described more fully below, the ventilator 10 provides a continuous flow rate of gas through the patient circuit during the inspiratory phase, and an equal or lower (but also continuous) "base" flow rate during the expiratory phase. During inspiration, the patient 26 inhales gas into his or her lungs (not shown) through the patient connector 24. During exhalation, the patient 26 exhales gas through the patient connector 24, from which the exhaled gas joins with the ventilator-generated base flow in the patient circuit, and this mixture of exhaled gas and base flow gas is conducted by the expiratory leg 22 to the exhalation valve 28.

The exhalation valve 28 includes an inlet 30 that receives gas from the expiratory leg 22, and an outlet vent 32 to the exterior of the ventilator 10. An expiratory flow path is thus defined by the expiratory leg 22 of the patient circuit, the exhalation valve inlet 30, and the exhalation valve outlet vent 32. The exhalation valve 28 also includes a proximal pressure port 33 that receives the patient's proximal airway pressure from the patient connector 24 through a proximal pressure sensing line 34, and a reference pressure port 35 that receives a reference pressure from a pressure reference subsystem 36, as will be described in detail below. A proximal pressure gauge and/or transducer 38 is advantageously coupled to the proximal pressure sensing line 34 to provide a visual indication of the proximal pressure.

Advantageously, the exhalation valve 28 is pneumatically servo-actuated, whereby proximal pressure is continuously directed to one side of an internal, differential pressure valving mechanism (not shown), while the reference pressure is directed to the other side. The valving mechanism blocks the portion of the expiratory flow path between the exhalation valve inlet 30 and the outlet vent 32 as long as the pressure differential (between the proximal pressure and the reference pressure) indicates that the proximal pressure is less than the reference pressure. When the pressure differential indicates that the proximal pressure is greater than the reference pressure, the valve mechanism responds by opening the expiratory flow path (typically by opening the outlet vent 32) with the degree of opening being proportional to the magnitude of the pressure differential. The opening of the expiratory flow path causes the proximal pressure directed to the exhalation valve 28 to fall, whereby the magnitude of the pressure differential across the valving mechanism decreases, thereby causing the degree of opening of the expiratory flow path to decrease proportionately.

The specific construction of the exhalation valve 28 is not a part of the present invention, and it may assume a number of functionally satisfactory embodiments. Furthermore, exhalation valves that would operate satisfactorily in the ventilator 10 are well known in the art. Therefore, a detailed description of such a valve is not necessary here. Briefly, in a preferred embodiment of the present invention, the exhalation valve 28 includes a first chamber in communication with the proximal pressure port 33, a second chamber in communication with the reference pressure port 35, a pressure-responsive element (such as a diaphragm) separating the two chambers, a valve closure member disposed between the inlet port 30 and the outlet vent 32, and a linkage mechanically connecting the pressure-responsive element with the closure member to provide the proportional opening function described above.

A currently-available exhalation valve, of the general type described above, is disclosed in U.S. Pat. No. 4,527,557, the disclosure of which is incorporated herein by reference. That patent, which is assigned to the assignee of the present invention, describes a device that employs a balloon-like pressure-responsive element, wherein the internal pressure in the balloon-like element is the reference pressure (termed "pilot pressure" in the patent), and the external pressure applied to this element is the proximal pressure.

Disposed within the patient connector 24 so as to receive the flow of gas therethrough is a flow sensor head 40. The flow sensor head 40 may be of any suitable type, such as a fixed or variable orifice pneumotachograph, an ultrasonic flow sensor, or a rotary element flow sensor, all of which are well-known in the art. In the preferred embodiment of the invention, the flow sensor head 40 is of the hot wire type. Examples of suitable hot wire flow sensors are disclosed in U.S. Pat. Nos. 4,363,238 and 5,263,369, and in co-pending U.S. patent application Ser. No. 08/273,888; filed Jul. 12, 1994; and assigned to the assignee of the present invention. In the preferred embodiment of the present invention, the flow sensor head 40 is of the type disclosed in the aforementioned U.S. patent application Ser. No. 08/273,888. A detailed description of this type of flow sensor head is set forth below in connection with FIG. 7 of the accompanying drawings.

The flow sensor head 40 generates an analog output signal indicative of the instantaneous gas flow rate through the patient connector 24. This flow rate signal, which has a value indicative of the instantaneous flow rate of gas inhaled and exhaled by the patient through the connector 24, is processed and conditioned by a flow sensor circuit 42. Suitable flow sensor circuits are well-known in the art, as represented, for example, by the aforementioned U.S. Pat. No. 5,263,369. In the preferred embodiment of the present invention, however, the flow sensor circuit 42 is of the type disclosed in the aforementioned U.S. patent application Ser. No. 08/273,888. A detailed description of this circuit is set forth below in connection with FIG. 8 of the accompanying drawings.

As more fully described below, when respiratory gas is delivered to the patient, the flow sensor circuit 42 produces a digitized inhalation flow rate signal and outputs it to a volume integration module 44 in a central processing unit (CPU) 46. The volume integration module 44 is a software module stored in a read only memory (ROM) 47 (FIG. 8) in the CPU 46. It employs a conventional algorithm to integrate the digitized inhalation flow rate signal over specified time intervals to obtain a measured volume value.

A volume limit control 48 on the ventilator 10 is manually operated by the clinician to select a volume limit from a predetermined range. The volume limit control 48 generates an analog volume limit signal that is fed to a first analog-to-digital converter (ADC) 50 in the CPU 46, which, in turn, digitizes the signal and outputs it to a volume limit setting module 52 in the CPU 46. The volume limit setting module 52 is a software module that stores the digitized value of the volume limit signal.

A volume comparator module 54 in the CPU 46 periodically reads the measured volume value from the volume integration module 44 and the volume limit value from the volume limit setting module 52, and then electronically compares these two values. The comparison yields a difference signal that is outputted to a breath control module 56 in the CPU 46.

The breath control module 56 is a software module that receives several input signals in addition to the above-mentioned difference signal. Specifically, it receives a breath rate signal, an inspiratory time signal, and an assist trigger signal. The breath rate signal is generated by a clinician-operated breath rate control 58 on the ventilator 10, and it is digitized by a second ADC 60 before being inputted to the breath control module 56. Its value represents the selected value of an adjustable breath rate, usually expressed in breaths per minute (BPM). The inspiratory time signal is generated by a clinician-operated inspiratory time control 62 on the ventilator 10, and it is digitized by a third ADC 64 before being inputted to the breath control module 56. Its value represents the selected length (duration) of an adjustable inspiratory time period. The assist trigger signal is generated by an assist trigger subsystem, which will be described below.

The breath control module includes an algorithm that reads the values of the aforementioned input signals, and generates a breath control signal that actuates a solenoid control/driver circuit 66. The solenoid control/driver circuit 66 responds to the breath control signal by generating first and second solenoid actuation signals that respectively actuate solenoid-actuated valves in the flow control subsystem 18 and in the pressure reference subsystem 36, as will be described below.

Figure 5:
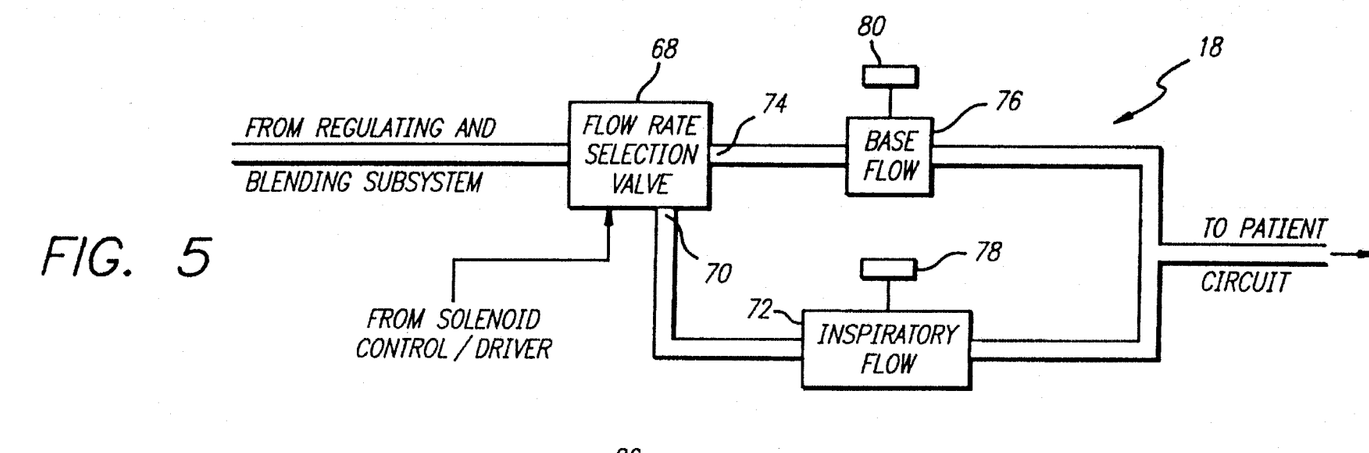
FIG. 5 is a schematic representation of the flow control subsystem employed in the ventilator of FIG. 4.

FIG. 5 illustrates the components and function of the flow control subsystem 18. Gas from the regulating and blending subsystem 16 is received in the inlet of a solenoid-actuated flow rate selection valve 68. The flow rate selection valve 68 has two outlets: a first outlet 70 communicates with the inlet of a clinician-adjustable inspiratory flow valve 72, and a second outlet 74 communicates with the inlet of a clinician-adjustable base flow valve 76. Either the first or second outlet of the flow rate selection valve 68 is opened in response to the first solenoid actuation signal generated by the solenoid control/driver circuit 66. The value of the first solenoid actuation signal thus determines which of the two flow rate selection valve outlets is opened, thereby determining whether the gas flows through the inspiratory flow valve 72 or the base flow valve 76. As will be explained more fully below, the first solenoid actuation signal actuates the flow rate selection valve 68 so as to open its first outlet 70 during the inspiratory phase, and its second outlet 74 during the expiratory phase.

The inspiratory flow valve 72 has an outlet that communicates with the inspiratory leg 20 of the patient circuit. This valve provides a substantially constant flow rate of inspiratory gas during the inspiratory phase, which flow rate can be adjusted by the clinician by means of an inspiratory flow rate control 78, which actuates a variable-orifice mechanism (not shown) of conventional design.

The base flow valve 76 likewise has an outlet that communicates with the inspiratory leg 20 of the patient circuit. This valve also provides a substantially constant flow rate of inspiratory gas, but the range of flow rates that it provides is typically equal to or lower than the range of flow rates provided by the inspiratory flow valve 72. This "base" flow rate is provided during the expiratory phase to allow the patient (typically an infant or neonate) to take small, spontaneous breaths outside of the preselected inspiratory time period. The base flow rate can be adjusted by the clinician by means of a base flow rate control 80, which actuates a variable orifice mechanism (not shown) of conventional design.

Figure 6:
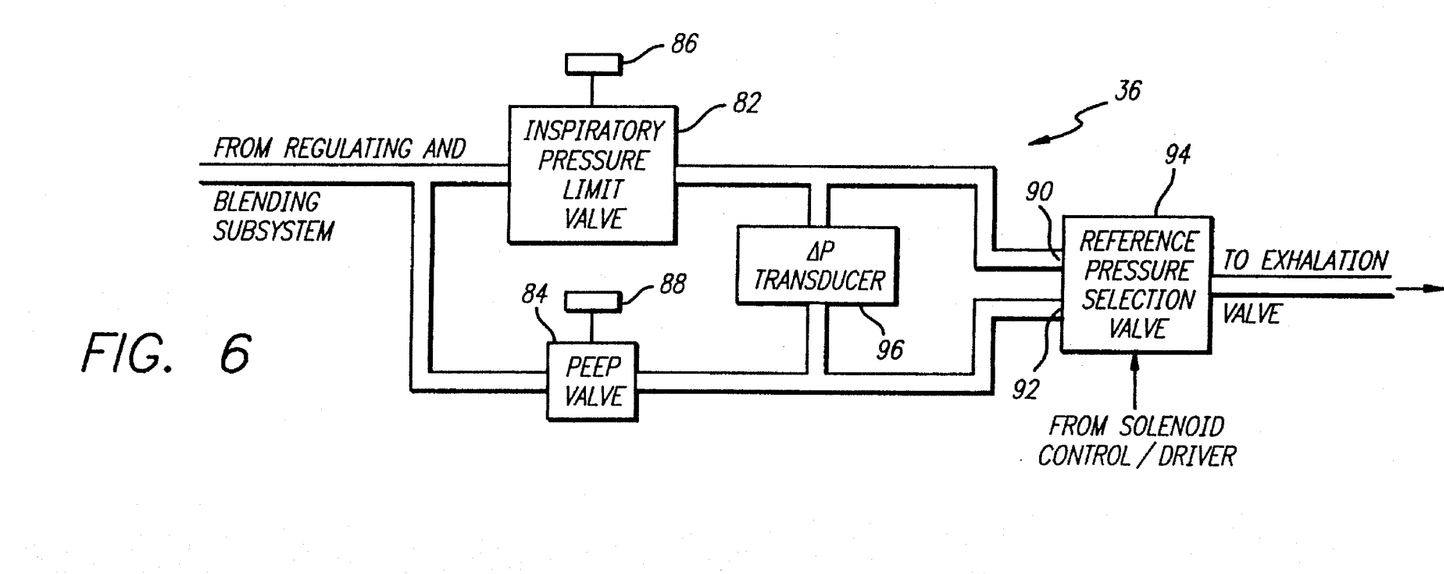
FIG. 6 is a schematic representation of the pressure reference subsystem employed in the ventilator of FIG. 4.

FIG. 6 illustrates the components and function of the pressure reference subsystem 36. Gas pressure (typically, the regulated air pressure) from the regulating and blending subsystem 16 is directed to the inlet port of a clinician-adjustable inspiratory pressure limit valve 82 and the inlet port of a clinician-adjustable PEEP adjustment valve 84. The inspiratory pressure limit valve 82 is adjusted by a pressure limit control 86 to select a peak inspiratory pressure (PIP) to be used as a first reference pressure for the actuation of the exhalation valve 28 during the inspiratory phase, thereby (as will be seen) providing the pressure relief function of the ventilator 10. The PEEP adjustment valve 84 is adjusted by a PEEP control 88 to select the PEEP value that is used as a second reference pressure for the exhalation valve 28 during the exhalation phase, as will be explained below. The selected PEEP reference value may typically be varied from zero PEEP (ambient pressure) to a maximum of about 30 cmH$_2$O (for an infant ventilator), or higher (for an adult ventilator).

The adjusted reference pressures from the respective outlets of the inspiratory pressure limit valve 82 and the PEEP adjustment valve 84 are communicated to a first inlet 90 and a second inlet 92, respectively, of a solenoid-actuated reference pressure selection valve 94. A differential pressure transducer 96 is advantageously disposed between the respective outlets of the inspiratory pressure limit valve 82 and the PEEP adjustment valve 84 so as to receive the selected PIP reference pressure on one side of the transducer 96, and the selected PEEP reference pressure on the other side. The transducer 96 compares the two reference pressures, and generates a warning device actuation signal if the PEEP reference pressure exceeds the PIP reference pressure. The warning device actuation signal, in turn, is employed to actuate a warning device, such as an audible and/or visible alarm (not shown).

The reference pressure selection valve 94 includes an outlet that communicates with the reference pressure port 35 of the exhalation valve 28, and (as mentioned above) the first inlet 90 that receives the PIP reference pressure and the second inlet 92 that receives the PEEP reference pressure. The reference pressure selection valve 94 responds to the second solenoid actuation signal generated by the solenoid control/driver circuit 66 to open either the first inlet 90 or the second inlet 92. The value of the second solenoid actuation signal thus determines which of the reference pressures (PIP reference pressure or PEEP reference pressure) is communicated, through the reference pressure selection valve 94, to the reference pressure port 35 of the exhalation valve 28.

Figures 7, 8:
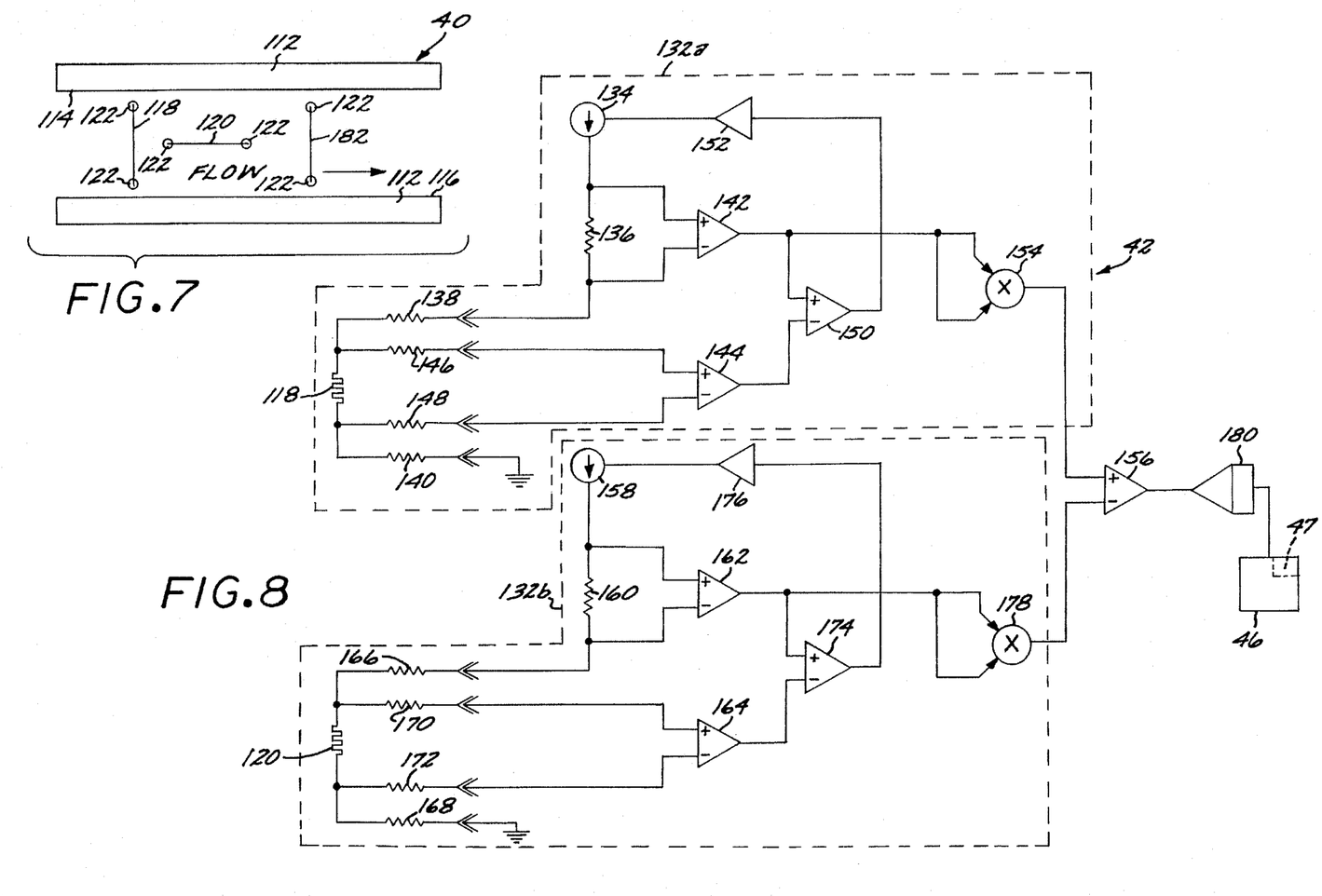
FIG. 7 is a diagrammatic representation of a hot wire flow sensor head, of the type used in a preferred embodiment of the present invention.
FIG. 8 is a schematic diagram of the electronic circuitry used in the preferred embodiment of the present invention to process the output signal from the flow sensor head of FIG. 7.

Referring now to FIG. 7, the hot wire flow sensor head 40, of the type employed in the preferred embodiment of the present invention, is shown diagrammatically. The flow head 40 comprises a tubular housing 112 having an open inlet end 114 and an open outlet end 116. Mounted within the housing 112 is a first thermoresistive wire element 118 mounted transversely to the direction of gas flow (indicated by the arrow), and a second thermoresistive wire element 120 mounted parallel to the direction of gas flow. The first or transverse wire element 118 may also be termed the "sensor" element, while the second or parallel wire element 120 may be termed the "reference" element, as will be made clear below. The wire elements 118, 120 may be supported within the housing 112 on insulative supports 122, with leads (not shown) extending through the housing wall for connection to the circuit to be described below.

The wire elements 118, 120 have identical thermoresistive characteristics, in that the sensing element 118 and the reference element 120 will exhibit the same resistance at any given temperature within a given temperature range. In a zero gas flow condition, the same current flowing through the two elements will result in equal power consumption by the two elements. When gas flows through the flow sensor head 40, however, the transverse sensor element 118 will experience a greater heat loss in response to the gas flow than will the parallel reference element 120 (as will be explained below), thereby lowering its resistance relative to the reference element. Therefore, to maintain the two wire elements at an equal temperature, the current must be increased through the sensor element 118, thereby increasing its power consumption relative to that of the reference element 120. The difference in power consumed by the sensor element and the reference element in maintaining the two elements at the same temperature is thus a function of the flow rate of the gas. Since both elements are located in close proximity to each other and are exposed to the same gaseous medium, variations in gas temperature, composition of the gas mixture, and humidity will have a negligible effect upon the resultant power differential. The function of the present invention, therefore, is to measure this power differential, and then relate it quantitatively to the flow rate of gas through the sensor head 40.

By nulling the no-flow power value $P_o$ for both wire elements 118, 120, and comparing the current in the two elements at a given, fixed temperature, the difference between the sensor element power $P_s$ and the reference element power $P_r$ needed to maintain that temperature in the two wire elements in response to gas flow can be ascertained, using the circuit described below.

FIG. 8 diagrammatically illustrates a preferred embodiment of the flow sensor circuit 42, from which is obtained an output signal indicative of the volumetric flow rate of gas through the flow sensor head 40. The flow sensor circuit 42 comprises a pair of ratiometric comparator circuits: a first comparator circuit 132a for the sensor element 118, and a second comparator circuit 132b for the reference element 120.

The first comparator circuit 132a includes a first current generator 134 that supplies current to the sensor element 118, thereby heating the sensor element 118. Connected in series between the first current generator 134 and the sensor element 118 is a first current sense resistor 136, which is a fixed resistance of known value. The heating current also passes through cables and connectors, schematically represented by series resistors 138 and 140. A first differential amplifier 142 is connected across the first current sense resistor 136, producing a first analog output signal having a voltage value that is related to the heating current supplied to the sensor element 118 by Ohm's Law (and by a known amplification factor). Thus, by knowing the output voltage and the amplification factor of the first amplifier 142 and the value of the first current sense resistor 136, the heating current through the first current sense resistor 136, and therefore the sensor element 118, can be measured.

Similarly, a second differential amplifier 144 is connected across the sensor element 118, and produces a second analog output signal having a value that is indicative of the voltage across the sensor element 118. Since the heating current through the sensor element 118 is known (by means of the output signal value from the first amplifier 142, as described above), the value of the output signal of the second amplifier 144 is indicative, via Ohm's Law, of the instantaneous resistance of the sensor element 118. (Additional cable and connector resistances, represented schematically by resistors 146 and 148 in the input leads of the second amplifier 144, may also be present in the circuit.)

The output signals from both the first amplifier 142 and the second amplifier 144 are fed into a third differential amplifier 150, which produces a third output signal having a voltage value that is proportional to the difference in the first and second output signal values. This third output signal, which is advantageously amplified by a fourth amplifier 152, is then fed back as an input to the first current generator 134 as a correction signal to adjust the heating current to a value which minimizes the difference between the first and second output signal values.

In other words, since the current through the first current sense resistor 136 is necessarily equal to the heating current through the sensor element 118, and since the resistance of the sensor element 118 is a known function of the heating current through it, the first comparator circuit 132a will be in balance when the value of the heating current is such as to make the resistance of the sensor element 118 equal to the fixed resistance of the first current sense resistor 136, thereby equalizing the voltage drops across the sensor element 118 and the first current sense resistor 136.

With the respective resistances of the first current sense resistor 136 and the sensor element 118 thus equalized to an equilibrium value which equals the known, fixed value of the first current sense resistor 136, and with the value of the heating current which produces this equilibrium state known (by the application of Ohm's Law to the voltage value of either the first or second output signals), the power $P_s$ delivered to the sensor element 118 is also known, by the formula:

$$P_s = I_s^2 R_1 \quad (2);$$

where $I_s$ is the heating current through the sensor element 118, and where $R_1$ is the resistance of the first current sense resistor 136.

Equivalently, sensor element power may be expressed as:

$$P_s = V_1^2 / R_1 \quad (2);$$

where $V_1$ is the voltage value of the first output signal.

Thus, the voltage value of the first output signal, when squared and divided by the resistance of the first sense resistor 136, provides an accurate measurement of the power delivered to the sensor element 118. Therefore, to obtain the squared value of the first output signal voltage, the first output signal is fed into a first squaring circuit 154, and this squared first output signal value is then inputted to a final differential amplifier 156 for final processing, as described below.

The cable and connector resistances (represented by the resistors 138, 140, 146, and 148) are not involved in the calculation of sensor element power $P_s$, and thus do not affect the measurement of this parameter.

It should be noted that it is not necessary for the operation of the circuit to require, for balancing the circuit, that the resistance of the sensor element 118 equal that of the first current sense resistor 136. This condition of resistance equality will result when the respective gains of the first amplifier 142 and the second amplifier 144 are equal. If the respective gains of the two amplifiers are not equal, but instead are related by a gain ratio, then the circuit is balanced when the ratio of the two resistances is the reciprocal of the gain ratio.

The second comparator circuit 132b for the reference element 120 is essentially identical to the first comparator circuit 132a described above. Thus, the second comparator circuit 132b comprises a second current generator 158 that supplies heating current to the reference element 120 through a second current sense resistor 160, of known, fixed value, equal to the value of the first current sense resistor. A fifth amplifier (differential amplifier) 162 is connected across the second current sense resistor 160, producing a fourth analog output signal having a voltage value that is related to the heating current value by Ohm's Law and the amplifier's gain. A sixth amplifier (differential amplifier) 164 is connected across the reference element 120, and produces a fifth analog output signal having a value that is indicative of the voltage across the reference element 120, and therefore, as explained above in connection with the second amplifier 144 and the sensor element 118, of the instantaneous resistance of the reference element 120. As described above for the first comparator circuit 132a, cable and connector resistances are shown schematically by fixed resistors 166, 168, 170, and 172.

The fourth and fifth output signals from the fifth amplifier 162 and the sixth amplifier, respectively, are fed into a seventh amplifier (differential amplifier) 174, which performs a function analagous to that of the third amplifier 150 of the first comparator circuit 132a: It produces a sixth output signal having a voltage value that is proportional to the difference in the fourth and fifth output signal values. This sixth output signal, which is advantageously amplified by an eighth amplifier 176, is then fed back as an input to the second current generator 158 as a correction signal to adjust the heating current through the reference element 120 to a value that minimizes the difference between the fourth and fifth output signal values.

The second comparator circuit 132b functions in a manner that is essentially identical to the operation of the first comparator circuit 132a. Thus, if the gains of the fifth amplifier 162 and the sixth amplifier 164 are equal, the circuit 132b is in balance when the value of the heating current through the reference element 120 is such as to make the resistance of the reference element 120 equal to an equilibrium value which equals the fixed resistance of the second current sense resistor 160, thereby equalizing the voltage drops across the reference element 120 and the second current sense resistor 160. Therefore, the power $P_r$ delivered to the reference element 120 can be expressed as:

$$P_r = I_r^2 R_2 \quad (3),$$

where $I_r$ is the heating current through the reference element 120, and where $R_2$ is the resistance of the second current sense resistor 160.

Equivalently, $P_r$ can be expressed as:

$$P_r = V_4^2 / R_2 \quad (4),$$

where $V_4$ is the voltage value of the fourth output signal.

Thus, the voltage value of the fourth output signal, when squared and divided by the resistance of the second sense resistor 160, provides an accurate measurement of the power delivered to the reference element 120. Therefore, to obtain the squared value of the fourth output signal voltage, the fourth output signal is fed into a second squaring circuit 178, and this squared fourth output signal value is then inputted to the final differential amplifier 156 for final processing.

The final differential amplifier 156 receives, as inputs, the squared first output signal and the squared fourth output signal, as described above, and compares these squared values to yield a final analog output signal that indicates the difference between the two squared values. This difference, which may be termed ΔP, represents the difference in the power respectively delivered to the sensor element 118 and the reference element 120 at any given flow rate of gas through the flow head 40. Mathematically, the value of the final analog output signal may be expressed as:

$$\Delta P = V_s^2/R_1 - V_r^2/R_2; \text{ or} \quad (5)$$

since $R_1 = R_2 = R$:

$$\Delta P = (V_s^2 - V_r^2)/R \quad (6)$$

The final analog output signal is fed into an analog-to-digital converter (ADC) 180, thereby digitizing the signal for input into the CPU 46. The ROM 47 of the CPU 46 has stored within it, in the form of a look-up table, the values corresponding to an empirically-derived flow rate-versus-delta power curve. Thus, the digitized ΔP value is used to address the look-up table, thereby acquiring the corresponding flow rate value, which is then outputted to the volume integration module 44 in the CPU 46.

The flow rate-versus-delta power curve that is stored in the ROM 47 can be empirically-derived for each individual flow sensor head 40 during the manufacturing process by constructing the flow sensor head 40 and the circuit 42, and then causing known flow rates of gas (controlled, for example, by a precision flow control system, of any suitable type known in the art) to flow through the flow sensor head 40. The values of ΔP corresponding to each desired flow rate value in the selected range are then measured (by conventional means) to derive the flow rate-versus-delta power curve. The values from this curve are then stored in the ROM 47. In this manner, each flow sensor system is individually pre-calibrated by the manufacturer prior to clinical usage, thereby eliminating the need for further calibration by the clinician, while also providing precise compensation for variations between individual flow sensing systems, due to, for example, the tolerances in the physical and electrical characteristics of the constituent components.

An example of a look-up table with values from an empirically-derived flow rate-versus-delta power curve is reproduced below, with $R_1 = R_2 = 5$ ohms.

| Power (mw) | Flow rate (Liter/min) |
|---|---|
| 2.1 | 0.0 |
| 26.5 | 0.1 |
| 31.0 | 0.2 |
| 35.3 | 0.3 |
| 38.5 | 0.4 |
| 45.1 | 0.6 |
| 51.4 | 0.8 |
| 61.0 | 1.2 |
| 69.6 | 1.6 |
| 82.4 | 2.4 |
| 94.2 | 3.2 |
| 113.5 | 4.8 |
| 129.5 | 6.4 |
| 154.9 | 9.6 |
| 173.4 | 12.8 |
| 205.0 | 19.2 |
| 229.9 | 25.6 |
| 269.3 | 38.4 |
| 273.0 | 40.0 |

The above table could easily be normalized or scaled so that a nulled delta power corresponds to zero flow rate.

The system described above is capable of achieving very high degrees of accuracy in flow rate measurement, even at low flow rates. For example, flow rate measurements with an accuracy of 1 per cent can be achieved, even at flow rates as low as 50 ml/min. Such high accuracy at low flow rates makes such a system particularly well-suited for use in mechanical pulmonary ventilation systems, which, like the present invention, is particularly well-adapted for use with neonates.

The flow sensor head 40 may advantageously be adapted for bi-directional flow rate measurements by providing a third thermoresistive wire element 182 that functions as a second sensor element. The third wire element 182, like the first wire element 118, is mounted transversely in the housing 116, on the opposite side of the parallel wire element 120 from the first wire element 118. The third wire element is connected in a third comparator circuit (not shown) which is essentially identical to the first comparator circuit 132a. The third comparator circuit, containing the third wire element 182, is employed when gas flow through the housing 116 is in the direction opposite to that indicated by the arrow in FIG. 7. Such a bi-directional flow sensor may be preferred in some application.

The operation of the ventilator 10 as a pressure-limited, time-cycled ventilator with volume-cycle override may now be easily understood with reference to FIGS. 4, 5, and 6.

The clinician selects a volume limit with the volume limit control 48; a breath rate with the breath rate control 58; and an inspiratory time period with the inspiratory time control 62. The digitized value of the volume limit is stored in the volume limit setting module 52, as previously described, while the digitized values of the breath rate and the inspiratory time period are stored in the breath control module 56, as also described above.

At the beginning of the inspiratory time period, at time $T_0$, the breath control module 56 sends a breath control signal having a first (inspiration initiation) value to the solenoid control/driver circuit 66. The solenoid control/driver circuit 66 responds to the inspiration initiation value of the breath control signal by generating the first and second solenoid actuation signals. The first solenoid actuation signal is directed to the solenoid of the flow rate selection valve 68 in the flow control subsystem 18. This signal has a first value that causes the flow rate selection valve 68 to open its first outlet 70 (and thus to close its second outlet 74), thereby directing gas from the regulating and blending subsystem 16, through the inspiratory flow valve 72, and into the inspiratory leg 20 of the patient circuit, with the inspiratory flow rate set by the inspiratory flow rate control 74.

The second solenoid actuation signal is directed to the solenoid of the reference pressure selection valve 94 in the pressure reference subsystem 36. This signal has a first value (not necessarily equal to the first value of the first solenoid actuation signal) that causes the reference pressure selection valve 94 to open its first inlet 90 (and thus to, close its second inlet 92), thereby applying the PIP (set by the inspiratory pressure limit valve 82) as the reference pressure at the reference pressure port 35 of the exhalation valve 28.

As a result of the above-described actuations of the flow rate selection valve 68 and the reference pressure selection valve 94, the patient 26 receives the selected inspiratory flow rate through the inspiratory leg 20 of the patient circuit and the patient connector 24, and the patient inhales from this flow. The patient's airway proximal pressure is communicated from the patient connector 24 to the proximal pressure port 33 of the exhalation valve 28 by the proximal pressure line 34. As long as the proximal pressure is less than the PIP reference pressure at the reference pressure port 34, the exhalation valve remains closed, and exhalation is impeded. Once the proximal pressure exceeds the PIP reference pressure, the exhalation valve 28 opens the expiratory flow path sufficiently, and for a sufficient time, in the manner described above, to relieve the excess pressure, maintaining the proximal pressure substantially at the limit established by the PIP reference pressure.

The above-described situation persists until either of two events occurs: (1) the preselected inspiratory time period elapses; or (2) the measured tidal volume of the patient reaches the preselected volume limit.

The digitized value of the preselected inspiratory time period is stored, as previously mentioned, in the breath control module 56. A timer (not shown) in the breath control module 56 is initiated at time $T_0$ and clocks the elapsed time. If the timer reaches a value equal to the stored inspiratory time period value, then the preselected inspiratory time period has elapsed without the tidal volume having reached the preselected volume limit. At this time (corresponding to the time $T_1$ in FIG. 3), the breath control module 56 sends a breath control signal having a second (inspiration termination) value to the solenoid control/driver circuit 66. The solenoid control/driver circuit 66 responds to the inspiration termination value of the breath control module output signal by sending the first and second solenoid actuation signals to the respective solenoids of the flow rate selection valve 68 and the reference pressure selection valve 94.

Now, however, the first solenoid actuation signal has a second value that causes the flow rate selection valve 68 to close its first outlet 70 and open its second outlet 74. Gas from the regulating and blending subsystem 16 is thus directed through the base flow valve 76, allowing only the preselected base flow to flow into inspiratory leg 20 of the patient circuit.

The second solenoid actuation signal also has a second value (not necessarily equal to the second value of the first solenoid actuation signal) that causes the reference pressure selection valve 94 to open its second inlet 92 and close its first inlet 90. As a result, the PEEP reference pressure from the PEEP control valve 84 is passed by the reference pressure selection valve 94 to the reference pressure port 35 of the exhalation valve 28.

As a result of the above-described actuations of the flow rate selection valve 68 and the reference pressure selection valve 94, the patient 26 receives the selected base flow rate through the inspiratory leg 20 of the patient circuit and the patient connector 24. The patient's airway proximal pressure is communicated from the patient connector 24 to the proximal pressure port 33 of the exhalation valve 28 by means of the proximal pressure line 34. As long as the proximal pressure is greater than the PEEP reference pressure at the reference pressure port 35, the exhalation valve is opened, allowing expiratory flow through the expiratory flow path, from the expiratory leg 22 of the patient circuit, through the inlet 30 of the exhalation valve 28, and out to ambient through the outlet vent 32 of the exhalation valve 28. Thus, the patient is permitted to exhale through the open exhalation valve 28, with the exhaled gasses from the patient joining the base flow from the ventilator. As the proximal pressure decreases during the expiratory phase, it approaches the PEEP reference pressure, and, as it does so, the exhalation valve 28 begins to close the expiratory flow path (by means of the above-described pneumatic servo operation) to a degree sufficient to maintain the proximal pressure at or above the PEEP reference pressure level. Thus, the patient exhales to the preselected PEEP reference pressure. Obviously, if the PEEP reference pressure is set to zero PEEP, the exhalation valve 28 remains fully open throughout the expiratory phase, and the patient exhales to ambient pressure.

As discussed above, during the inspiratory phase, the volume integration module 44 receives a digitized inhalation flow rate signal from the flow sensor circuit 42, and integrates the value of this signal over time to obtain a measured tidal volume value. This measured tidal volume value is compared, in the volume comparison module 54, with the digitized volume limit value generated by the volume limit setting module 52. This comparison yields the above-mentioned difference signal which is inputted to the breath control module 56. If the value of the difference signal indicates that the measured tidal volume is less than the preselected volume limit, then the breath control signal outputted by the breath control module 56 is unaffected. If, on the other hand, the difference signal indicates that the measured tidal volume is equal to or greater than the preselected volume limit, then the breath control module 56 generates a breath control signal having the second (inspiration termination) value, causing the solenoid control/driver circuit 66 to generate its first and second solenoid actuation signals having their respective second values. As described above, when the first and second solenoid actuation signals having their respective second values are received by the solenoids of the flow rate selection valve 68 and the reference pressure selection valve 94, respectively, the ventilator 10 terminates the inspiratory flow (and shifts to the base flow), and opens the exhalation valve 28 (with the preselected PEEP value as the reference pressure).

Thus, the inspiratory phase is terminated at the time $T_{V_L}$ shown in the graph I of FIG. 3, which is before the end of the preselected inspiratory time period. The expiratory phase is therefore commenced in response to the patient's tidal volume reaching the preselected volume limit, rather than in response to the elapsing of the preselected inspiratory time period.

The value of the breath rate signal generated by the breath rate control 58 is stored in memory (not shown) in the breath control module 56. The value of the breath rate signal defines the time period for the periodic reinitiation of the inspiratory time period; that is, it defines the period of repetition of the inspiratory/respiratory breath cycle described above. At the reinitiation of the inspiratory time period, the ventilator is returned to the conditions existing at the time $T^{\wedge}_0$, as described above.

Referring again to FIG. 4, the ventilator 10 is advantageously provided with an assist mode capability, provided by an assist trigger module 98. The assist trigger module 98 is a software module stored in a ROM (not shown) in the CPU 46. It contains an algorithm for providing a machine-assisted breath to the patient under certain specified conditions.

Specifically, the assist trigger module 98 receives the digitized inhalation flow rate signal from the flow sensor circuit 42, along with a digitized assist level signal. The assist level signal is generated as an analog signal by a clinician-operated assist sensitivity control 100, and this analog signal is digitized by a fourth ADC 102. The assist level signal has a value representing a minimum inhalation flow rate necessary for triggering an assisted breath.

The digitized assist level signal value and the digitized measured inhalation flow rate value are compared in the assist trigger module 98. If the measured flow rate value is greater than the assist level signal value, the algorithm in the assist trigger module then determines if the ventilator is in an "assist disabled" period. The assist disabled period comprises the inspiratory time period, plus a selectable beginning portion of the expiratory time period. Only during the remainder of the expiratory time period can the assist mode be enabled.

If the ventilator is not in the assist disabled period, the algorithm next determines if the assist trigger "window" is open; that is, if the ventilator's operational mode would, at that point in the breath cycle, permit the ventilator to provide a machine-assisted breath. If the "window" is open, the assist trigger module 98 generates an assist trigger output signal that is inputted to the breath control module 56. The breath control module 56, in turn, responds by sending a control signal having the first (inspiration initiation) value to the solenoid control driver circuit 66, which, in turn, responds by generating the first and second solenoid actuation signals having their respective first values, as described above. As a result, as also described above, the first and second solenoid actuation signals actuate the flow rate selection valve 74 to select the inspiratory flow rate, and the reference pressure selection valve 94 to select the PIP reference pressure. The result of these actuations is to cause the ventilator to deliver a machine-assisted breath to the patient.

If, on the other hand, the trigger "window" is not open, the algorithm determines if the ventilator is in either a CPAP (Continuous Positive Airway Pressure) or SIMV (Synchronous Intermittent Mandatory Ventilation) mode. If it is in either of these modes, a spontaneous breath count register (not shown) is incremented, but no assist trigger output signal is generated.

The ventilator system described above will be seen to provide the advantages of a pressure-limited, time-cycled ventilator, with the additional advantages provided by the volume-cycle override feature, of which the most prominent is the effective management of the above-described problems associated with changes in the patient's airway compliance. In particular, the novel approach of integrating a volume-cycle override function into a pressure-limited, time-cycled ventilator provides an easily implemented regimen for controlling the ventilation process so as to compensate automatically for compliance changes in a manner that does not require frequent monitoring or adjustment of the ventilator's operational parameters, thereby facilitating the use of such a ventilator in the clinical environment.

While a preferred embodiment of the invention has been described above, it will be appreciated that certain modifications and variations will suggest themselves to those skilled in the pertinent arts. For example, the present invention may be employed in a pressure-limited, time-cycled ventilator that provides the same selected flow rate during both the inspiratory phase and the expiratory phase, rather than having a different base flow rate during the expiratory phase. Furthermore, the flow rate sensing system and the exhalation valve system described above are exemplary only, and functionally suitable alternatives may suggest themselves. Likewise, the assist mode function may be provided by alternatives to the system described above, or even omitted altogether, if desired. These and other variations that may suggest themselves to the skilled practitioner in the pertinent arts should be considered within the spirit and scope of the present invention, as defined in the claims that follow.

What is claimed is:

1. A method for the pulmonary ventilation of a human patient, comprising the steps of:

(a) selecting an inspiratory time period, an inspiratory flow rate, a peak inspiratory pressure limit, and an inspiratory tidal volume limit;

(b) at the beginning of the inspiratory time period, providing a flow of respiratory gas to the patient at the selected inspiratory flow rate, while impeding an expiratory flow from the patient;

(c) limiting the peak inspiratory pressure during inspiration to the selected peak inspiratory pressure limit;

(d) measuring the inspiratory tidal volume of the patient during the inspiratory time period;

(e) (1) periodically comparing the measured inspiratory tidal volume to the selected inspiratory tidal volume limit during the inspiratory time period; and (e) (2) ceasing to impede the expiratory flow from the patient when the selected inspiratory time period elapses or when the selected tidal volume limit is reached, whichever first occurs.

2. The method of claim 1, wherein the step of measuring the inspiratory tidal volume comprises the steps of:

(d) (1) measuring the instantaneous inhalation flow rate of the patient and generating a flow rate-indicative signal; and (d) (2) integrating the flow rate-indicative signal over time to obtain a measured tidal volume value.

3. The method of claim 2, wherein the expiratory flow from the patient is controlled by an exhalation valve, and wherein the step of ceasing to impede the expiratory flow comprises the steps of:

generating an exhalation valve control signal when the measured tidal volume value is greater than or equal to the selected tidal volume limit; and actuating the exhalation valve in response to the exhalation valve control signal so as to permit expiratory flow therethrough.

4. The method of claim 1, wherein the step of selecting includes the step of selecting a breath rate that defines a periodic reinitiation of the inspiratory time period, and wherein at the reinitiation of the inspiratory time period, the step of ceasing to impede the expiratory flow is terminated, and the steps of providing the flow of respiratory gas to the patient at the inspiratory flow rate, limiting the peak inspiratory pressure, and measuring the tidal volume are repeated.

5. The method of claim 1, wherein the step of selecting includes the step of selecting a base flow rate; wherein the step of providing a flow of respiratory gas at the selected inspiratory flow rate is performed only during the selected inspiratory time period and only when the measured tidal volume is less than the selected tidal volume limit; and wherein the method further comprises the step of:

(f) providing a flow of respiratory gas to the patient at the selected base flow rate during the step of ceasing to impede the expiratory flow from the patient.

6. An improved ventilator, of the type including a pressurized gas system having means for supplying a flow of respiratory gas to a patient at a selected inspiratory flow rate during a selected inspiratory time period, and an exhalation valve mechanism having means for (a) opening an expiratory flow path from the patient in response to the elapsing of the inspiratory time period and (b) maintaining a selected proximal pressure limit during the inspiratory time period, wherein the improvement comprises:

a volume-cycle override means for actuating the exhalation valve mechanism so as to open the expiratory flow path if the measured tidal volume of a patient reaches or exceeds a selected volume limit value during the inspiratory time period.

7. The improved ventilator of claim 6, wherein the volume-cycle override means further comprises:

a tidal volume measuring means for producing a first signal indicative of the measured tidal volume of a patient during the inspiratory time period;

a volume limit setting means for producing a second signal indicative of a selected adjustable volume limit value;

a comparator means for comparing the first and second signals and generates a difference signal indicative of the difference between the measured tidal volume and the selected volume limit value; and an exhalation control means for actuating the exhalation valve mechanism to open the expiratory flow path in response to the difference signal having a value indicative of the measured tidal volume being equal to or greater than the selected volume limit value.

8. The improved ventilator of claim 7, wherein the tidal volume measuring means further comprises:

a flow sensor disposed so as to measure the inhalation flow rate of the patient, and providing a flow rate signal indicative of the inhalation flow rate; and an integrator means for integrating the flow rate signal over time to obtain the first signal, and that outputs the value of the first signal to the comparator means.

9. The improved ventilator of claim 7, wherein the volume limit setting means further comprises:

an adjustable volume limit controlling means that is actuable for selecting the selected volume limit, and that generates the second signal; and a memory means for storing the value of the second signal for outputting to the comparator means.

10. The improved ventilator of claim 6, wherein the improvement further comprises:

an assisted breath means for actuating the exhalation valve mechanism to close the expiratory path, and for actuating the pressurized gas system to provide the flow of respiratory gas at the selected inspiratory flow rate, in response to an inhalation flow rate that equals or exceeds a selected assist level during a selected expiratory time interval that commences after the inspiratory time period has elapsed.

11. The improved ventilator of claim 10, wherein the assisted breath means further comprises:

a flow sensor that generates a flow rate signal having a value indicative of the inhalation flow rate of the patient;

an assist sensitivity control means for selecting the assist level, and that generates an assist level signal having a value indicative of the selected assist level; and an assist trigger means, responsive to the flow rate signal and the assist level signal, for actuating the exhalation valve mechanism to close the expiratory path, and for actuating the pressurized gas system to provide the flow of respiratory gas at the selected inspiratory flow rate, when the inhalation flow rate value equals or exceeds the selected assist level value during the selected expiratory time interval.

12. A volume-cycled override control system for a pressure-limited, time-cycled medical ventilator, of the type including a pressurized gas delivery system that provides a respiratory gas to a patient at a selected inspiratory flow rate, and an exhalation valve system that (a) opens an expiratory flow path from the patient in response to the elapsing of a selected inspiratory time period and (b) maintains a selected peak inspiratory pressure limit during the inspiratory time period, the volume-cycled override control system comprising:

a flow sensor, coupled between the patient and the ventilator, that generates a flow rate signal having a value indicative of the inhalation flow rate of the patient;

an integrator means, responsive to the flow rate signal, for generating a tidal volume signal having a value indicative of the instantaneous tidal volume of the patient;

an adjustable volume limit setting means for generating a selected volume limit value;

a comparator means for comparing the tidal volume value and the selected volume limit value and for generating a difference signal having a value indicative of the difference between the tidal volume value and the selected volume limit value; and an exhalation control means for actuating the exhalation valve system to open the expiratory flow path before the inspiratory time period has elapsed in response to the difference signal having a value indicative of the measured tidal volume being equal to or greater than the selected volume limit value.

13. The volume-cycled override control system of claim 12, wherein the exhalation valve system comprises:

a pressure reference means for providing a selected reference pressure;

a proximal pressure conduit receiving proximal pressure from the patient; and an exhalation valve having an inlet that receives expiratory flow from the patient, an outlet vent, a proximal pressure port in fluid communication with the proximal pressure conduit to receive the proximal pressure therefrom, and a reference pressure port in fluid communication with the pressure reference means to receive the reference pressure therefrom, wherein a portion of the expiratory flow path is defined between the inlet and the outlet vent;

wherein the valve is opened to allow expiratory gas to flow from the inlet to the outlet vent in response to a proximal pressure that is greater than the selected reference pressure.

14. The volume-cycled override control system of claim 13, wherein the pressure reference subsystem includes means that are actuable in response to a first value of a reference pressure selection signal for providing an adjustable peak inspiratory pressure as a first reference pressure, and in response to a second value of the reference pressure selection signal for providing an adjustable positive end expiratory pressure as a second reference pressure.

15. The volume-cycled override control system of claim 14, wherein the exhalation control means further comprises:

an adjustable inspiratory time control means for generating an inspiratory time signal having a value indicative of the selected inspiratory time period; and a control means that responds to the inspiratory time signal and to the difference signal for generating the reference pressure selection signal having the first value at the beginning of the inspiratory time period and the second value at the end of the inspiratory time period or when the difference signal has a value indicative of the measured tidal volume being greater than or equal to the selected volume limit value, whichever first occurs.

16. The volume-cycled override control system of claim 15, wherein the pressure reference means further comprises:

a peak inspiratory pressure limiting means for providing the first reference pressure;

a positive end expiratory pressure means for providing the second reference pressure; and a reference pressure selection means for passing the first reference pressure to the reference pressure port of the exhalation valve in response to the first value of the reference pressure selection signal, and for passing the second reference pressure to the reference pressure port of the exhalation valve in response to the second value of the reference pressure selection signal.

17. The volume-cycled override control system of claim 12, further comprising:

a flow control means for providing the respiratory gas to the patient at the selected inspiratory flow rate during the selected inspiratory time period, and for providing the respiratory gas to the patient at a selected base flow rate when the exhalation valve system opens the expiratory flow path.

18. The volume-cycled override control system of claim 17, wherein the flow control subsystem includes means that are actuable in response to a first value of a flow rate selection signal for providing a flow of respiratory gas to the patient at the selected inspiratory flow rate, and in response to a second value of the flow rate selection signal for providing a flow of respiratory gas to the patient at the selected base flow rate.

19. The volume-cycled override control system of claim 18, further comprising:

an adjustable inspiratory time control for generating an inspiratory time signal having a value indicative of the selected inspiratory time period; and a control means for generating the flow rate selection signal in response to the inspiratory time signal and to the difference signal and having the first value at the beginning of the inspiratory time period and the second value at the end of the inspiratory time period or when the difference signal has a value indicative of the measured tidal volume being greater than or equal to the selected volume limit value, whichever first occurs.

20. The volume-cycled override control system of claim 19, wherein the flow control means further comprises:

an inspiratory flow rate valve means for providing a flow of respiratory gas to the patient at the selected inspiratory flow rate;

a base flow rate valve means for providing a flow of respiratory gas to a patient at the selected base flow rate; and a flow rate selection means for passing the respiratory gas through the inspiratory flow rate valve in response to the first value of the flow rate selection signal, and for passing the respiratory gas through the base flow rate valve in response to the second value of the flow rate selection signal.

21. A medical ventilator system for providing time-cycled, pressure-limited ventilation of a patient, comprising:

a respiratory gas delivery means for (a) for providing a flow of respiratory gas to the patient at a selected inspiratory flow rate in response to a first value of a control signal, and at a selected base flow rate in response to a second value of the control signal, and (b) providing a reference pressure having a first reference pressure value in response to the first value of the control signal, and a second reference pressure value in response to the second value of the control signal;

an inspiratory time control means for generating an inspiratory time signal having a value indicative of a selected inspiratory time period;

a tidal volume measuring means for producing a tidal volume signal having a value indicative of the measured tidal volume of the patient during the inspiratory time period;

a volume limit setting means for producing a volume limit signal having a value indicative of a selected volume limit;

a comparator means for comparing the tidal volume signal value with the volume limit signal value, and that generates a difference signal indicative of the difference between the tidal volume signal value and the volume limit signal value;

a breath control means that responds to the inspiratory time signal and the difference signal for generating the control signal having the first value at the beginning of the selected inspiratory time period, and for generating the control signal having the second value at the end of the inspiratory time period or when the difference signal has a value indicative of the measured tidal volume being equal to or greater than the selected volume limit, whichever first occurs; and an exhalation valve system that receives proximal pressure from the patient and the reference pressure, and that opens an expiratory flow path from the patient when the proximal pressure exceeds the reference pressure value provided by the gas delivery system.

22. The medical ventilator system of claim 21, wherein the gas delivery means comprises:

a flow control means for providing a flow of respiratory gas to a patient at the selected inspiratory flow rate in response to the first value of the control signal, and for providing a flow of respiratory gas to a patient at the selected base flow rate in response to the second value of the control signal; and a pressure reference means that responds to the first value of the control signal for providing a reference pressure having the first reference pressure value, and to the second value of the control signal by providing a reference pressure having the second reference pressure value.

23. The medical ventilator of claim 22, wherein the flow control means comprises:

an inspiratory flow rate valve means for providing a flow of respiratory gas to the patient at the selected inspiratory flow rate;

a base flow rate valve means for providing a flow of respiratory gas to the patient at the selected base flow rate; and a flow rate selection means for passing the respiratory gas through the inspiratory flow rate valve in response to the first value of the control signal, and for passing the respiratory gas through the base flow rate valve in response to the second value of the control signal.

24. The medical ventilator of claim 22, wherein the pressure reference means comprises:

a peak inspiratory pressure limiting means for providing the first reference pressure value;

a positive end expiratory pressure means for providing the second reference pressure value; and a reference pressure selection means for passing the first reference pressure value to the exhalation valve system in response to the first value of the control signal, and for passing the second reference pressure value to the exhalation valve system in response to the second value of the control signal.

25. The medical ventilator system of claim 21, wherein the tidal volume measuring means comprises:

a flow sensor disposed so as to measure the inhalation flow rate of the patient, and providing a flow rate signal indicative of the inhalation flow rate; and an integrator means for integrating the flow rate signal over time to obtain the tidal volume signal, and for outputting the value of the tidal volume signal to the comparator.

26. The medical ventilator system of claim 25, wherein the volume limit setting means further comprises:

an adjustable volume limit control means for selecting the selected volume limit, and for generating the volume limit signal; and a memory means for storing the value of the volume limit signal for outputting to the comparator.

27. The medical ventilator system of claim 21, further comprising:

an assisted breath system having means for actuating the exhalation valve system to close the expiratory path, and for actuating the gas delivery system to provide the flow of respiratory gas at the selected inspiratory flow rate, in response to an inhalation flow rate that equals or exceeds a selected assist level during a selected expiratory time interval that commences after the inspiratory time period has elapsed.

28. The medical ventilator system of claim 27, wherein the assisted breath system comprises:

a flow sensor that generates a flow rate signal having a value indicative of the inhalation flow rate of the patient;

an assist sensitivity control means for selecting the assist level and for generating an assist level signal having a value indicative of the selected assist level; and an assist trigger means, responsive to the flow rate signal and the assist level signal, for actuating the exhalation valve system to close the expiratory path, and for actuating the gas delivery system to provide the flow of respiratory gas at the selected inspiratory flow rate, when the inhalation flow rate value equals or exceeds the selected assist level value during the selected expiratory time interval.

* * * * *